United States Patent [19]

Green

[11] 4,360,476

[45] Nov. 23, 1982

[54] METHOD OF CONCENTRATING A SOLUTION OF METHYLENE DIPHENYL DIISOCYANATE IN DIPHENYL OXIDE

[75] Inventor: John G. Green, Baton Rouge, La.

[73] Assignee: The Dow Chemical Company, Midland, Mich.

[21] Appl. No.: 334,402

[22] Filed: Dec. 24, 1981

[51] Int. Cl.³ .................................... C07C 119/048
[52] U.S. Cl. ...................... 260/453 SP; 260/453 P; 260/453 AM
[58] Field of Search .............. 260/453 SP, 453 AM, 260/453 P

[56] References Cited

U.S. PATENT DOCUMENTS

| | | | |
|---|---|---|---|
| 1,899,257 | 2/1933 | Britton et al. | 568/609 |
| 2,552,523 | 5/1951 | Cunningham | 62/124 |
| 2,617,274 | 11/1952 | Schmidt | 62/124 |
| 3,054,819 | 9/1962 | Barclay, Jr. et al. | 260/453 |
| 3,591,617 | 7/1971 | Buchsbaum | 260/453 |

FOREIGN PATENT DOCUMENTS 7306235  4/1972  Netherlands .

*Primary Examiner*—Dolph H. Torrence
*Attorney, Agent, or Firm*—A. J. Young

[57] ABSTRACT

A method of concentrating a solution of methylene diphenyl diisocyanate in diphenyl oxide, which includes cooling the solution until part of the solution crystallizes, thereby forming a solid phase having a lower concentration of the methylene diphenyl diisocyanate, and a liquid phase having a higher concentration of the methylene diphenyl diisocyanate than in the original solution, and then separating the solid and liquid phases. The method is particularly applicable to the concentration of solutions of 4,4'-methylene diphenyl diisocyanate in diphenyl oxide.

4 Claims, No Drawings

METHOD OF CONCENTRATING A SOLUTION OF METHYLENE DIPHENYL DIISOCYANATE IN DIPHENYL OXIDE

BACKGROUND OF THE INVENTION

This invention relates to a method of concentrating solutions of methylene diphenyl diisocyanate. More particularly, this invention relates to a method of concentrating solutions of methylene diphenyl diisocyanate in diphenyl oxide.

The compound 4,4'-methylene diphenyl diisocyanate is an extremely important intermediate for the production of polyurethanes. Commercially, this compound may be made by the thermal decomposition of 4,4'-methylene dimethyl diphenyldicarbamate, preferably as a dilute solution in diphenyl oxide, whereby the reaction mixture contains both the desired diisocyanate product and unreacted dicarbamate. Therefore, in this process, it is necessary to provide a method of separating the diisocyanate from unreacted dicarbamate and solvent or diluent. However, prior to separation of the desired diisocyanate product, the reaction mixture needs to be concentrated with respect to the desired product, 4,4'-methylene diphenyl diisocyanate, because of the large amount of diluent in the reaction mixture.

Prior-art methods for concentrating solutions of methylene diphenyl diisocyanate generally include distillation of the solvent. Such distillation requires rather high temperatures, whereby the desired product is subject to undesirable thermal degradation or formation of higher polymers; or comparitively high vacuum, which adds to the expense of the distillation step while reducing the efficiency thereof. It is therefore important to provide a method of separation which is not subject to these disadvantages.

SUMMARY

In general, the present invention provides a method of concentrating a solution of methylene diphenyl diisocyanate in diphenyl oxide, which comprises the steps of (a) cooling the solution until part of the solution crystallizes, thereby forming a solid phase with a lower concentration of the methylene diphenyl diisocyanate and a liquid phase with a higher concentration of the methylene diphenyl diisocyanate than in the original solution; and (b) separating the solid and liquid phases.

It is an object of this invention to provide a method for concentrating a solution of methylene diphenyl diisocyanate in diphenyl oxide. It is a further object of the invention to provide a method therefor which avoids thermal degradation or higher polymer formation of or from the methylene diphenyl diisocyanate, or the need to use a high vacuum. Other objects of the invention will be apparent to those skilled in the art from the more detailed description which follows.

DESCRIPTION OF THE PREFERRED EMBODIMENT

The following description illustrates the manner in which the principles of the present invention are applied, but is not to be construed as in any sense limiting the scope of the invention.

In concentrating a solution of methylene diphenyl diisocyanate in diphenyl oxide according to the method of the present invention, the solution is cooled to a temperature that is preferably in the range of between about 20° C. and about 30° C. It is beneficial to agitate the solution while it is beig cooled, and also while crystallization is occurring. After crystallization has occurred to the extent required to form a liquid phase of the desired concentration, the solid and liquid phases are separated by any one of several methods known in the art. The phases may be separated, for example, by settling, decantation, filtration, or centrifugation; or, if desired, a combination of two or more of these methods. The supernatant liquid phase is then recovered as the desired concentrated solution of methylene diphenyl diisocyanate. The method of the present invention is particularly well suited for concentrating solutions of 4,4'-methylene diphenyl diisocyanate in diphenyl oxide.

The invention will now be further illustrated by means of the following examples, which are illustrative only and which are not intended to limit in any way the scope of the invention.

EXAMPLE 1

A solution containing five grams of methylene diphenyl diisocyanate in one hundred grams of diphenyl oxide was allowed to fractionally crystallize for about four hours at room temperature, at a temperature between 20° and 30° C. The crystals were separated from the mother liquor by filtration. The crystals, which were not washed to remove residual mother liquor, weighted 40.1 grams, and contained 0.8 grams of methylene diphenyl diisocyanate per hundred grams of diphenyl oxide. The mother liquor weighed 60.4 grams, and contained 7.7 grams of methylene diphenyl diisocyanate per hundred grams of diphenyl oxide.

EXAMPLE 2

A solution containing five grams of 4,4'-methylene diphenyl diisocyanate in one hundred grams of diphenyl oxide was crystallized at room temperature as in Example 1, but in this second example the crystallization was carried out over a period of about twenty hours. The mother liquor, after separation from the crystals, was found to contain 10.5 grams of 4,4'-methylene diphenyl diisocyanate per hundred grams of diphenyl oxide.

While certain representative embodiments and details have been shown for the purpose of illustrating the present invention, it will be apparent to those skilled in the art that various changes and modifications can be made therein without departing from the spirit and scope of the invention.

What is claimed is:

1. A method of concentrating a solution of methylene diphenyl diisocyanate in diphenyl oxide, which comprises the steps of:
   (a) cooling the solution until part of the solution crystallizes, thereby forming a solid phase with a lower concentration of the methylene diphenyl diisocyanate and a liquid phase with a higher concentration of the methylene diphenyl diisocyanate than in the original solution; and
   (b) separating the solid and liquid phases.
2. The method of claim 1, wherein the solution is cooled to a temperature between about 20° C. and about 30° C.
3. The method of claim 1, wherein the methylene diphenyl diisocyanate is 4,4'-methylene diphenyl diisocyanate.
4. The method of claim 2, wherein the methylene diphenyl diisocyanate is 4,4'-methylene diphenyl diisocyanate.

* * * * *